United States Patent [19]

Clemence et al.

[11] Patent Number: 4,736,033

[45] Date of Patent: Apr. 5, 1988

[54] CERTAIN 1,3-DIHYDRO-1-[HETEROCYCLIC)IMINO]-FURO-[3,4-B]QUINOLINE 9-OL COMPOUNDS HAVING ANALGESIC AND ANTI-INFLAMMATORY ACTIVITY

[75] Inventors: Francois Clemence; Odile Le Martret, both of Paris; Françoise Delevallee, Fontenay sous Bois, all of France

[73] Assignee: Roussel Uclaf, Paris, France

[21] Appl. No.: 945,777

[22] Filed: Dec. 23, 1986

Related U.S. Application Data

[60] Continuation-in-part of Ser. No. 743,792, Jun. 12, 1985, abandoned, which is a division of Ser. No. 623,430, Jun. 22, 1984, Pat. No. 4,596,875, which is a division of Ser. No. 498,832, May 27, 1983, Pat. No. 4,486,438.

[30] Foreign Application Priority Data

Jun. 3, 1982 [FR] France ................ 82-09654

[51] Int. Cl.$^4$ .................................. C07D 491/048
[52] U.S. Cl. .................................. 546/89; 544/333; 546/156
[58] Field of Search .................. 546/89; 544/333

[56] References Cited

U.S. PATENT DOCUMENTS 4,397,856 8/1983 Allais et al. .................. 514/312

Primary Examiner—Alan L. Rotman
Attorney, Agent, or Firm—Bierman and Muserlian

[57] ABSTRACT

A 4-hydroxy-3-quinoline-carboxamides of the formula

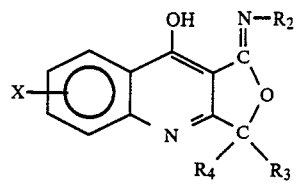

wherein X is in the 5,6,7 or 8-position and is selected from the group consisting of hydrogen, halogen, alkyl of 1 to 5 carbon atoms, alkoxy of 1 to 4 carbon atoms, —CH$_3$, —OCF$_3$ or —SCF$_3$, R$_1$ is selected from the group consisting of hydrogen and alkyl of 1 to 4 carbon atoms, R$_2$ is selected from the group consisting of a heterocycle connected to the nitrogen by a carbon atom selected from thiazolyl, 4,5-dihydro-thiazolyl, pyridinyl, oxazolyl, isoxazolyl, imidazolyl, pyrimidinyl or tetrazolyl, all optionally substituted with alkyl of 1 to 4 carbon atoms or phenyl optionally substituted with at least one member of the group consisting of —OH, alkyl of 1 to 4 carbon atoms, alkoxy of 1 to 4 carbon atoms, —CH$_3$, —NO$_2$ or halogen, R$_3$ is selected from the group consisting of hydrogen, alkyl of 1 to 4 carbon atoms or aryl, R$_4$ is selected from the group consisting of hydrogen, alkyl of 1 to 4 carbon atoms or aryl, and their non-toxic, pharmaceutically acceptable acid addition salts and salts with non-toxic, pharmaceutically acceptable bases having very good analgesis activity and a non-negligible anti-inflammatory activity and novel intermediates.

1 Claim, No Drawings

CERTAIN 1,3-DIHYDRO-1-[HETEROCYCLIC)IMINO]-FURO-[3,4-B]QUINOLINE 9-OL COMPOUNDS HAVING ANALGESIC AND ANTI-INFLAMMATORY ACTIVITY

CROSS REFERENCE TO PRIOR APPLICATIONS

This application is a continuation-in-part of U.S. patent application Ser. No. 743,792 filed June 12, 1985 abandoned, which is a division of U.S. patent application Ser. No. 623,430 filed June 22, 1984 now U.S. Pat. No. 4,596,875 which is a division of U.S. patent application Ser. No. 498,832 filed May 27, 1983 now U.S. Pat. No. 4,486,438.

STATE OF THE ART

Commonly assigned U.S. Pat. Nos. 4,299,831 and 4,107,310 and commonly assigned U.S. patent application Ser. No. 262,952 filed May 12, 1981, now U.S. Pat. No. 4,397,856 described various 3-quinoline-carboxamides of different structure.

OBJECTS OF THE INVENTION

It is an object of the invention to provide the novel compounds of formula I and their non-toxic, pharmaceutically acceptable salts and a novel process and intermediates for their preparation.

It is another object of the invention to provide novel analgesic and anti-inflammatory compositions and a novel method of treating pain and inflammation in warm-blooded animals.

These and other objects and advantages of the invention will become obvious from the following detailed description.

THE INVENTION

The novel compounds of the invention are selected from the group consisting of 4-hydroxy-3-quinoline-carboxamides of the formula

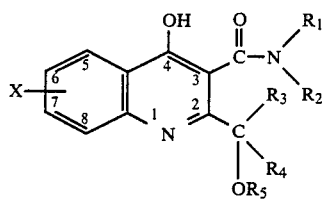

wherein X is in the 5, 6, 7 or 8-position and is selected from the group consisting of hydrogen, halogen, alkyl of 1 to 5 carbon atoms, alkoxy of 1 to 4 carbon atoms, —CF$_3$, —OCF$_3$ and —SCF$_3$, R$_1$ is selected from the group conisting of hydrogen and alkyl of 1 to 4 carbon atoms, R$_2$ is selected from the group consisting of heterocycles connected to the nitrogen atom through a carbon atom as follows

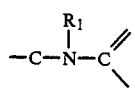

including thiazolyl, 4,5-dihydro-thiazolyl, pyridinyl, oxazolyl, isoxazolyl, imidazolyl, pyrimidinyl and tetrazolyl, all optionally substituted with alkyl of 1 to 4 carbon atoms and phenyl optionally substituted with at least one member of the group consisting of —OH, alkyl of 1 to 4 carbon atoms, alkoxy of 1 to 4 carbon atoms, —CF$_3$, —NO$_2$ and halogen, R$_3$ is selected from the group consisting of hydrogen, alkyl of 1 to 4 carbon atoms and aryl, R$_4$ is selected from the group consisting of hydrogen, alkyl of 1 to 4 carbon atoms and aryl, R$_5$ is selected from the group consisting of hydrogen, alkyl of 1 to 4 carbon atoms and

R$_5'$ is selected from the group consisting of alkyl of 1 to 4 carbon atoms and aryl and their non-toxic, pharmaceutically acceptable acid addition salts and salts with non-toxic, pharmaceutically acceptable bases.

Examples of X are halogens such as bromine, fluorine and preferably chlorine and alkyl such as methyl, ethyl, n-propyl, n-butyl, isopropyl, n-pentyl and isobutyl, alkoxy such as methoxy, ethoxy or n-propoxy. When R$_1$ is alkyl, it is preferably methyl or ethyl.

When R$_2$ is an alkyl substituted heterocycle, the alkyl is preferably methyl or ethyl and when R$_2$ is a substituted phenyl, the substituent is preferably at least one member of the group consisting of —OH, methyl, ethyl, methoxy, ethoxy, —NO$_2$, —CF$_3$ and chlorine.

When R$_3$ is alkyl, it is preferably methyl, ethyl, propyl, isopropyl, butyl or isobutyl and when R$_3$ it aryl, it is preferably phenyl or naphthyl. When R$_4$ is alkyl, it is preferably methyl, ethyl, propyl, isopropyl, butyl or isobutyl and when R$_4$ is aryl, it is preferably phenyl or naphthyl.

When R$_5$ is alkyl, it is preferably methyl or ethyl and when R$_5$ is

R$_5'$ is preferably methyl or ethyl when it is alkyl or phenyl when it is aryl.

Examples of suitable acids for the formation of non-toxic, pharmaceutically acceptable acid addition salts are inorganic acids such as hydrochloric acid, hydrobromic acid, nitric acid, sulfuric acid or phosphoric acid, alkanesulfonic acids such as methanesulfonic acid and arylsulfonic acids such as p-toluene sulfonic acid. Examples of suitable bases for the formation of salts are alkali metal bases such as sodium or potassium hydroxide or amines such as trimethylamine or dimethylamine.

Among the preferred compounds of formula I are those wherein X is in the 8-position and especially when X is —CF$_3$, those wherein R$_1$ is hydrogen, those wherein R$_2$ is thiazolyl, those wherein R$_3$, R$_4$ and R$_5$ are hydrogen, those wherein R$_5$ is alkyl of 1 to 4 carbon atoms and those wherein R$_3$ is hydrogen, R$_4$ is alkyl and R$_5$ is hydrogen or

and their salts with non-toxic, pharmaceutically acceptable acids and bases.

Specific preferred compounds are 2-(1-acetyloxyethyl)-4-hydroxy-N-(2-thiazolyl)-8-trifluoromethyl-3- quinoline-carboxamide, 4-hydroxy-2-(1-hydroxyethyl)-N-(2-thiazolyl)-8-trifluoromethyl-3-quinoline-carboxamide and 4-hydroxy-2-(1-hydroxypropyl)-N-(2-thiazolyl)-8-trifluoromethyl-3-quinoline-carboxamine and their salts with non-toxic, pharmaceutically acceptable acids and bases.

The novel process for the preparation of compounds of formula I wherein $R_5$ is hydrogen or

comprises reacting a compound of formula

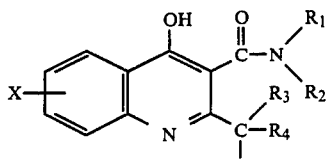

wherein X, $R_1$, $R_2$, $R_3$ and $R_4$ have the above definitions and X' is a halogen with a salt of an acid of the formula

   A wherein $R_5'$ is alkyl of 1 to 4 carbon atoms or aryl to obtain a compound of formula I wherein $R_5$ is

and, if desired, treating the latter with an acid hydrolysis agent to obtain a compound of formula I wherein $R_5$ is hydrogen which optionally can be reacted with a base or acid to obtain the corresponding salt.

Preferably, X' is chlorine and the acid of formula A is an alkali metal salt such as the sodium or potassium salt. The acid hydrolysis is preferably effected with hydrochloric acid but other acids such as sulfuric acid may be used. The reaction is preferably effected in an alcoholic or aqueous alcoholic medium such as methanol, ethanol or propanol or in an aqueous acetone medium.

The novel process of the invention for the preparation of compounds of formula I wherein $R_5$ is alkyl of 1 to 4 carbon atoms comprises reacting a compound of the formula

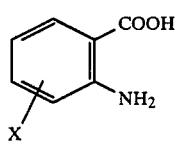   III wherein X has the above definition with an acid of the formula

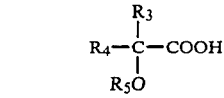   IV wherein $R_3$ and $R_4$ have the above definition and $R_5$ is alkyl of 1 to 4 carbon atoms or a functional derivative of the acid to obtain a compound of the formula

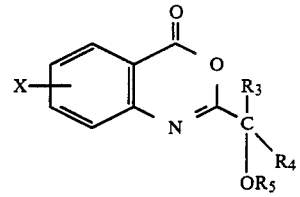   V reacting the latter with a compound of the formula

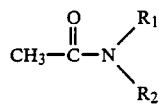   VI wherein $R_1$ and $R_2$ have the above definition to obtain a compound of the formula

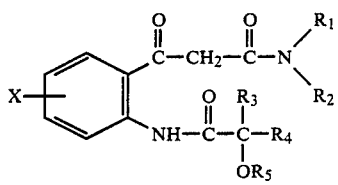   VII and cyclizing the latter in the presence of an alkaline agent to obtain the corresponding compound of formula I wherein $R_5$ is alkyl of 1 to 4 carbon atoms and optionally reacting the latter with a base or acid to form the corresponding salt.

In a preferred mode of the process of the invention, the functional derivative of the acid of formula IV is an acid halide or anhydride and the reaction between the compounds of formulae V and VI is effected in the presence of an organolithium or a lithium amide such as in the presence of butyllithium or lithium diisopropylamide. The cyclization of the compound of formula VII is preferably effected in the presence of an alkali metal agent such as alkali metal hydride or carbonate or an amine such as sodium hydride, sodium carbonate, potassium carbonate, piperidine, 4-dimethylaminopyridine, 4-amino-pyridine, triethylamine, 1,5-diazabicyclo[4,3,0]non-5ene, 1,4-diazabicyclo[2,2,2]octane or 1,5-diazabicyclo[5,4,0]undec-5-ene.

In a modification of the process of the invention, a compound of formula I wherein $R_3$, $R_4$ and $R_5$ are hydrogen may be prepared by reacting a compound of formula I wherein $R_3$ and $R_4$ are hydrogen and $R_5$ is alkyl of 1 to 4 carbon atoms with a boron trihalide to obtain the desired compound of formula I which may be salified with an acid or base.

Preferably the boron trihalide is boron trichloride or boron tribromide and the reaction is effected in a chlorinated solvent such as methylene chloride, but other solvents such as 1,1-dichloroethane, chloroform or carbon tetrachloride may be used and the preferred temperature is about −70° C.

In a modification of the process in the invention, a compound of formula I wherein $R_1$ and $R_5$ are hydrogen may be prepared by reacting a compound of the formula

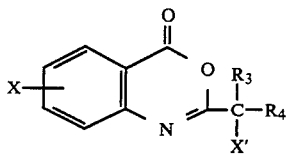

VIII wherein X, X', $R_3$ and $R_4$ have the above definitions with a compound of the formula

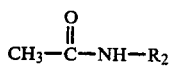

IX to obtain a compound of the formula

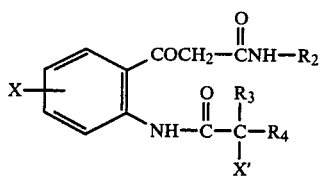

X cyclizing the latter with an alkali metal agent to obtain intermediarily a compound of the formula

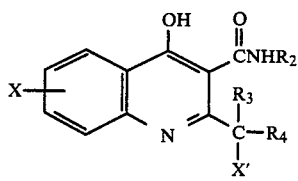

XI which is optionally isolated or which become to obtain a compound of the formula

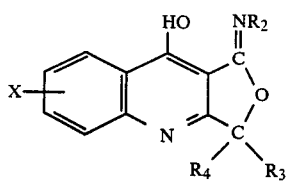

XII and treating the latter with an acid hydrolysis agent to obtain the compound of formula I wherein $R_1$ and $R_5$ are hydrogen which may be salified with an acid or base.

In a modification of the latter process of the invention, the compound of formula X is reacted at room temperature with an alkaline agent to preferentially obtain the compound of the formula XI or with an alkaline agent at a more elevated temparture to preferentially obtain the compound of formula XII. In a variant of the latter process the compound of the formula XI is isolated and reacted with an acid agent to obtain the compound of formula XII.

Preferably, X' is chlorine and the reaction of the compounds of formulae VIII and IX is effected in the presence of an organolithium or a lithium amide such as in the presence of butyllithium or lithium diisopropylamide. The cyclization of the compound of formula X is preferably effected in the presence of an alkaline agent such as alkali metal hydrides or carbonates or amines like sodium hydride, sodium carbonate, potassium carbonate, piperidine, 4-aminopyridine, 4-dimethylaminopyridine, triethylamine, 1,5-diazabicyclo[4,3,0]non-5-ene, 1,4-diazabicyclo[2,2,2]octane or 1,5-diazabicyclo[5,4,0]undec-5-ene and is effected in a solvent such as tetrahydrofuran, but other solvents such as dimethylformamide, benzene or toluene may be used. To obtain the compound of formula XII directly, the reaction is effected at reflux temperature. The acid hydrolysis agent is preferably hydrochloric acid but other acids such as sulfuric acid may be used. When the product of formula XII is obtained by cyclization of the isolated compound of formula XI, the preferred acid agent is acetic acid but other acids such as hydrochloric acid or sulfuric acid may be used.

The novel analgesic and anti-inflammatory compositions of the invention are comprised of an analgesically and anti-inflammatorily effective amount of at least one compound of formula I and its non-toxic, pharmaceutically acceptable salts and an inert pharmaceutical carrier or excipient. The compositions may be in the form of tablets, dragees, gelules, granules, suppositories, injectable solutions or suspensions, pomades, creams, gels and aerosol preparations formed in the usual fashion.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

The compositions are useful for the treatment of muscular, articular or nervous pain, dental pain, rhumatismatic affections, zona, and migraines as well as for the treatment of inflammatory conditions, especially arthrosis, lumbagos as well as a complementary treatment for infections and feverish states.

Among the preferred compositions of the invention are those wherein the active ingredient is selected from the group consisting of 2-(1-acetyloxyethyl)-4-hydroxy-N-(2-thiazolyl)-8-trifluoromethyl-3-quinoline-carboxamide, 4-hydroxy-2-(1-hydroxyethyl)-N-(2-thiazolyl)-8-trifluoromethyl-3-quinoline-carboxamide and 4-hydroxy-2-(1-hydroxypropyl)-N-(2-thiazolyl)-8-trifluoromethyl-3-quinoline-carboxamide and their salts with non-toxic, pharmaceutically acceptable acids and bases.

The novel method of the invention for relieving pain and inflammation in warm-blooded animals, including humans, comprises administering to warm-blooded animals an analgesically and anti-inflammatorily effective amount of at least one compound of formula I and its non-toxic, pharmaceutically acceptable salts. The compounds may be administered orally, rectally, parenterally or topically to the skin or mucous. The usual effective dose is dependent on the specific compound and the method of administration, and the conditions treated and may be 0,25 to 25 mg/kg per day in the adult by oral route.

Some of the compounds of formula II, VIII, X and XI are described and prepared in copending U.S. patent application Ser. No. 262,952 filed May 12, 1981 and those not prepared and described can be prepared by the said process.

The compounds of formula III are generally known and may be prepared by the process of French Pat. No. 2,157,874 for example.

The compounds of formulae V and VII and XII are novel compounds and are an object of the invention. Certain compounds of formulae VIII and X are not claimed in the said copending U.S. patent application such as 2-[chlorobenzyl]-8-trifluoromethyl-4H-3,1-benzoxazine-4-one, 2-[2-chloro-2-phenylacetamido]-$\beta$-oxo-N-(2-thiazolyl)-3-trifluoromethylbenzene-propanamide, and are also an object of the invention.

In the following examples there are described several preferred embodiments to illustrate the invention. However, it should be understood that the invention is not intended to be limited to the specified embodiments.

EXAMPLE 1

2-(1-acetyloxy-ethyl)-4-hydroxy-N-(2-thiazolyl)-8-trifluoromethyl-3-quinoline-carboxamide A mixture of 4 g of 2-(1-chloroethyl)-4-hydroxy-N-(2-thiazolyl)-8-trifluoromethyl-3-quinoline-carboxamide [described in Examples 5 and 14 of U.S. patent application Ser. No. 262,952 filed May 12, 1981], 40 ml of acetic acid and 1.23 g of anhydrous potassium acetate was stirred at reflux for 90 minutes and was then cooled to room temperature and poured into 200 ml of iced water. The mixture stood overnight and was then vacuum filtered. The product was washed with water and dried under reduced pressure at 90° C. to obtain 3.2 g of product. The latter was taken up in refluxing dioxane and the mixture was filtered hot. The filtrate was iced and the product was washed with water and dried under reduced pressure at 80° C. to obtain 1.3 g of 2-(1-acetyloxy-ethyl)-4-hydroxy-N-(2-thiazolyl)-8-trifluoromethyl-3-quinoline-carboxamide melting at 262° C.

Analysis: $C_{18}H_{14}N_3O_4F_3S$ Calculated: %C 50.82, %H 3.32, %N 9.88, %F 13.40, %S 7.54. Found: %C 51.0, %H 3.3, %N 9.7, %F 13.3, %S 7.5.

EXAMPLE 2

4-hydroxy-2-(1-hydroxyethyl)-N-(2-thiazolyl)-8-trifluoromethyl-3-quinoline-carboxamide A mixture of 4.3 g of the product of Example 1, 50 ml of ethanol of 25 ml of concentrated hydrochloric acid was refluxed with stirring for one hour and was then cooled and iced and vacuum filtered. The product was washed and dried under reduced pressure at 60° C. The said product was added to 300 ml of water and the mixture was extracted with ethyl acetate. The organic phase was washed with water, dried and filtered. The filtrate was evaporated to dryness under reduced pressure and the residue was crystallized from ethyl acetate. The mixture was iced and vacuum filtered and the recovered product was washed and dried under reduced pressure at 60° C. to obtain 2.45 g of 4-hydroxy-2-(1-hydroxyethyl)-N-(2-thiazolyl)-8-trifluoromethyl-3-quinoline-carboxamide melting at 205° C. and then at 235° C.

Analysis: $C_{16}H_{12}O_3N_3F_3S$ Calculated: %C 50.13, %H 3.16, %N 10.96, %F 14.87, %S 8.36. Found: %C 50.3, %H 3.1, %N 10.9, %F 14.7, %S 8.5.

EXAMPLE 3

4-hydroxy-2-methoxymethyl-N-(2-thiazolyl)-8-trifluoromethyl-3-quinoline-carboxamide

STEP A:

2-methoxymethyl-8-trifluoromethyl-4H-3,1-benzoxazine-4-one

A mixture of 7.1 g of 2-amino-3-trifluoromethylbenzoic acid [prepared by the process of J. Med. Chem., Vol. 16 (2) (1973), p. 101–106] and 10 g of methoxy acetic acid chloride was progressively heated and at 35° to 40° C., a very important disengagement of gas occurred for 15 to 20 minutes and at 120° C. a brown solution was formed and gas disengagement slackened but continued. The temperature was maintained at 140° C. for one hour during which gas formation practically ceased. The mixture was cooled to room temperature and excess acid chloride was distilled under reduced pressure. The residue was taken up in 70 ml of water and the mixture was vacuum filtered. The product was washed with water and was dissolved in methylene chloride. The organic phase was dried and filtered and the filtrate was evaporated to dryness under reduced pressure. The residue was chromatographed over silica gel and eluted with methylene chloride to obtain 5.4 g of 2-methoxymethyl-8-trifluoromethyl-4-H-3,1-benzoxazine-4-one melting at 104° to 106° C.

Analysis: $C_{11}H_8O_3NF_3$ Calculated: %C 50.97, %H 3.11, %N 5.40, %F 21.99. Found: %C 51.2, %H 3.1, %N 5.3, %F 22.3.

STEP B:

2-methoxyacetamido-$\beta$-oxo-N-(2-thiazolyl)-3-trifluoromethyl-benzene-propenamide 150 ml of a solution of 1.5 moles of butyllithium per liter of hexane were added over 20 minutes at 0° C. to a solution of 15.73 g of N-(2-thiazolyl)-acetamide in 550 ml of tetrahydrofuran and the mixture was stirred at 0° C. for 10 minutes and was cooled to −70° C. A solution of 14.4 g of the product of Step A in 165 ml of tetrahydrofuran was added at −70° C. over 15 minutes to the mixture which was then stirred at −70° C. for 30 minutes and poured into a mixture of ice and N hydrochloric acid. The mixture was extracted with ether and the combined organic phases were washed successively with hydrochloric acid and water, dried and evaporated to dryness under reduced pressure at 20° to 30° C. The residue was empasted with 250 ml of ether and was vacuum filtered. The product was washed with ether and dried under reduced pressure at 20° C. to obtain 15 g of 2-methoxyacetamido-$\beta$-oxo-N-(2-thiazolyl)-3-trifluoromethyl-benzene-propanamide melting at 152° C.

Analysis: $C_{16}H_{14}N_3F_3O_4S$ Calculated: %C 47.88, %H 3,52, %N 10.47, %S 7.99, %F 14.25. Found: %C 48.1, %H 3.6, %N 10.2, %S 8.2, %F 14.6.

STEP C:

4-hydroxy-2-methoxymethyl-N-(2-thiazolyl)-8-trifluoromethyl-3-quinoline-carboxamide 5.03 g of 4-dimethylamino-pyridine were added to a solution of 16.5 g of the product of Step B in 205 ml of tetrahydrofuran and the mixture was stirred at 20° C. for 4½ hours. The tetrahydrofuran was distilled off under reduced pressure at 40° C. and the dry residue was taken up in 500 ml of water. 42 ml of N hydrochloric acid were added to the mixture and the suspension was stirred at 20° C. for 30 minutes and was vacuum filtered. The product was washed with water, dried under reduced pressure at 70° C. and was crystallized from 310 ml of dioxane. The mixture was vacumm filtered at 15° C. and the product was washed with 30 ml of dioxane and dried under reduced pressure at 70° C. to obtain 13.3 g of 4-hydroxy-2-methoxymethyl-N-(2-thiazolyl)-8-trifluoromethyl-3-quinoline-carboxamide melting at 260° C.

Analysis: $C_{16}H_{12}F_3N_3O_3S$ Calculated: %C 50.13, %H 3.16, %N 10.96, %F 14.87, %S 8.36. Found: %C 50.3, %H 3.1, %N 10.8, %F 14.5, %S 8.4.

EXAMPLE 4

4-hydroxy-2-hydroxymethyl-N-(2-thiazolyl)-8-trifluoromethyl-3-quinoline-carboxamide A solution of 4 ml of boron tribomide in 30 ml of methylene chloride was added with stirring at −70° C. to a solution of 2.88 g of the product of Example 3 in 75 ml of methylene chloride and the mixture stood overnight with stirring while the temperature was allowed to rise to −20° C. The mixture was poured into 500 ml of ice and water and the mixture was stirred for 20 minutes and was vacuum filtered. The product was washed with water until the pH was 5 to 6 and was dried under reduced pressure at 100° C. The product was dissolved in refluxing dimethylformamide and the solution was cooled, iced and vacuum filtered. The product was washed with dimethylformamide and then with ether and dried under reduced pressure at 120° C. to obtain 2.3 g of 4-hydroxy-2-hydroxymethyl-N-(2-thiazolyl)-8-trifluorometyl-3-quinoline-carboxamide melting at 280° C.

Analysis: $C_{15}H_{10}O_3N_3F_3S$ Calculated: %C 48.78, %H 2.73, %N 11.38, %F 15.43, %S 8.68. Found: %C 48.5, %H 2.6, %N 11.5, %F 15.1, %S 9.0.

EXAMPLE 5

4-hydroxy-2-hydroxybenzyl-N-(2-thiazolyl)-8-trifluoromethyl-3-quinoline-carboxamide

STEP A:

2-chlorobenzyl-8-trifluoromethyl-4H-1,3-benzoxazin-4-one 12.3 g of 2-amino-3-trifluoromethyl-benzoic acid [prepared by process of J. Med. Chem., Vol. 16(2) (1973), p. 101–106] were added in small portions at room temperature to 30.25 g of DL α-chloro-phenylacetic acid chloride with stirring and the mixture was progressively heated for two hours. Gas disengagement was observed at 70° to 80° C. and then a mass formed and the mixture became fluidized and became a solution at about 140° C. and gas disengagement ceased. Excess acid chloride was distilled off and the residue was twice chromatographed over silica gel. Elution with methylene chloride yielded a brown oil which was empasted with petroleum ether. The mixture was vacuum filtered and the product was washed with petroleum ether and dried under reduced pressure at room temperature to obtain a 15.2 g of 2-chlorobenzyl-8-trifluoromethyl-4H-1,3-benzoxazin-4-one melting towards 85°–88° C.

STEP B:

2-(2-chloro-2-phenylacetamido)-β-oxo-N-(2-thiazolyl)-3-trifluoromethyl-benzene-propanamide 28.6 ml of a solution of 1.4 moles of n-butyllithium per liter of hexane were added at 0° C. to a solution of 2.84 g of N-(2-thiazolyl)-acetamide in 100 ml of tetrahydrofuran and 3.39 g of the product of Step A were added to the mixture cooled to −70° C. The mixture was poured into ice and N hydrochloric acid and was extracted with ether. The organic phase was washed successively with N-hydrochloric acid and with water, dried and evaporated to dryness under reduced pressure. The residue was empasted with 50 ml of ether and was vacuum filtered. The product was washed and dried under reduced pressure at 50° C. to obtain 3.2 g of 2-(2-chloro-2-phenylacetamido)-β-oxo-N-(2-thiazolyl)-3-trifluoromethyl-benzenepropanamide melting at 185° C. (decomposition).

STEP C:

1,3-dihydro-3-phenyl-1-[(2-thiazolyl)-imino]-5-trifluoromethyl-furo[3,4-b]quinoline-9-ol 1.82 g of 4-dimethylamino-pyridine were added to a solution of 6 g of the product of Step B in 150 ml of tetrahydrofuran and the mixture was stirred at room temperature for 16 hours and was evaporated to dryness under reduced pressure. The residue was extracted with 100 ml of water and 3 ml of hydrochloric acid were added to the aqueous extract which was stirred at room temperature for 15 minutes and was vacuum filtered. The product was washed with water and dried under reduced pressure at 90° C. to obtain 5.34 g of 1,3-dihydro-3-phenyl-1-[(2-thiazolyl)-imino]-5-trifluoromethyl-furo[3,4-b]quinoline-9-ol melting at 270° C. (decomposition).

STEP D:

4-hydroxy-2-hydroxybenzyl-N-(2-thiazolyl)-8-trifluoromethyl-3-quinoline-carboxamide A mixture of 4.2 g of the product of Step C, 150 ml of water and 75 ml of concentrated hydrochloric acid was refluxed with stirring for 45 minutes and was cooled to room temperature and iced and vacuum filtered. The product was washed with water and dried to obtain 4.2 of 4-hydroxy-2-hydroxybenzyl-N-(2-thiazolyl)-8-trifluoromethyl-3-quinoline-carboxamide hydrochloride melting at 210° C.

The said salt was added to 200 ml of water and the mixture was stirred at room temperature for one hour and was vacuum filtered. The product was washed with water and dried under reduced pressure at 100° C. The product was dissolved in 400 ml of acetonitrile and the solution was filtered through activated carbon. The filtrate was concentrated under reduced pressure and was iced for 16 hours and vacuum filtered. The product was washed and dried under reduced pressure at 80° C. to obtain 3.050 g of 4-hydroxy-2-hydroxybenzyl-N-(2-thiazolyl)-8-tifluoromethyl-3-quinoline-carboxamide melting at 240° C.

Analysis: Calculated: %C 56.63, %H 3.17, %N 9.43, %F 12.80, %S 7.20. Found: %C 56.4, %H 3.1, %N 9.4, %F 12.8, %S 7.3.

EXAMPLE 6

4-hydroxy-2-(2-hydroxyethyl)-N-(2-pyridinyl)-8-trifluoromethyl-3-quinoline-carboxamide

STEP A:

2-[(2-chloro-1-oxo-propyl)-amino]-β-oxo-N-(2-pyridinyl)-3-trifluoromethyl-benzene-propanamide 14 ml of a solution of butyllithium in hexane were added under argon at −5° to 0° C. over 30 minutes to a solution of 1.36 g of N-(2-pyridinyl)-acetamide in 27.2 ml of tetrahydrofuran and the mixture was stirred under argon at −5° C. for 15 minutes and was then cooled to −70° C. A solution of 1.38 g of 2-(1-chloromethyl)-8-trifluoromethyl-4H-3,1-benzoxazine-4-one [prepared in Step A of Example 14 of U.S. patent application Ser. No. 262,952] in 13.8 ml of tetrahydrofuran was added at −70° C. under argon over 30 minutes to the mixture which was stirred at −70° C. for one hour and was poured into a mixture of 200 ml of iced water and 10 ml of concentrated hydrochloric acid. The mixture was stirred at room temperature for 30 minutes and was extracted three times with 100 ml of ethyl acetate. The combined organic phases were washed twice with 75 ml of water, dried and evaporated to dryness under reduced pressure. The residue was chromatographed over silica gel and eluted with an 8-2 ethyl acetate-cyclohexane mixture. The product was taken up in ether and the mixture was filtered. The product was dried to obtain 1.2 g of 2-[(2-chloro-1-oxo-propyl)-amino]-β-oxo-N-(2-pyridinyl)-3-trifluoromethyl-benzene-propanamide melting towards 150° C.

STEP B:
1,3-dihydro-3-methyl-1-[(2-pyridinyl)-imino]-5-trifluoromethyl-furo[3,4-b]quinoline-9-ol 1.60 g of 4-dimethylamino-pyridine were added to a suspension of 4.5 g of the product of Step A in 90 ml of tetrahydrofuran and the mixture was refluxed for four hours and was evaporated to dryness under reduced pressure. The residue was added to 90 ml of water and the mixture was stirred for 30 minutes and was vacuum filtered. The product was washed with water and dried under reduced pressure at 70° C. to obtain 4.50 g of 1,3-dihydro-3-methyl-1-[(2-pyridinyl)-imino]-5-trifluoromethyl-furo[3,4-b]quinoline-9-ol which was crystallized from absolute ethanol.

Analysis: Calculated: %C 60.17, %H 3.37, %N 11.69, %F 15.86. Found: %C 60.2, %H 3.4, %N 11.5, %F 15.6.

STEP C:
4-hydroxy-2-(1-hydroxyethyl)-N-(2-pyridinyl)-8-trifluoromethyl-3-quinoline-carboxamide A mixture of 32 ml of 6N hydrochloric acid and 3.2 g of the product of Step B was stirred at room temperature for one hour and was vacuum filtered. The product was washed with water and dried under reduced pressure at 80° C. The product was empasted with 52 volumes of hot absolute ethanol and was vacuum filtered. The filtrate was concentrated to 20 volumes and cooled to 0° C. The product was crystallized from 25 volumes of absolute ethanol and the mixture was vacuum filtered. The filtrate was concentrated to 5 volumes and was cooled to 0° C. The product was chromatographed over silica gel and eluted with a 9-1 chloroform-methanol mixture to obtain 1 g of 4-hydroxy-2-(1-hydroxyethyl)-N-(2-pyridinyl)-8-trifluoromethyl-3-quinoline-carboxamide.

Analysis: Calculated: %C 57.30, %H 3.74, %N 11.14, %F 15.10. Found: %C 57.0, %H 3.8, %N 10.9, %F 14.9.

EXAMPLE 7

4-hydroxy-2-(1-hydroxyethyl)-N-(2-thiazolyl)-3-quinoline-carboxamide

STEP A: 2-(1-chloroethyl)-4H-3,1-benzoxazine-4-one 17.47 ml of 2-chloropropionic acid chloride were added with stirring at room temperature to a solution of 10.3 g of 2-amino-benzoic acid in 20 ml of toluene and the mixture was progressively heated to 65° C. during which a mass was formed and gas disengaged and the mixture fluidized. The mixture was held at reflux for 90 minutes and was evaporated to dryness under reduced pressure. The residue was empasted with petroleum ether (b.p.=60° to 80° C.), was iced and vacuum filtered. The product was washed and dried under reduced pressure at 50° C. to obtain 14.45 g of 2-(1-chloroethyl)-4H-3,1-benzoxazine-4-one melting at 90° C.

STEP B:
2-[(2-chloro-1-oxo-propyl)-amino]-β-oxo-N-(2-thiazolyl)-benzene-propanamide 191 ml of a solution of 1.4M of n-butyllithium per liter of hexane were added under argon at 0° C. to a solution of 19.05 g of N-(2-thiazolyl)-acetamide in 580 ml of tetrahydrofuran and then a solution of 14.04 g of the product of Step A in 100 ml of tetrahydrofuran were added thereto at −70° to −75° C. The mixture was poured into a mixture of water and 2N hydrochloric acid and the mixture was vacuum filtered. The product was washed with water and dried under reduced pressure to obtain 16.6 g of 2-[(2-chloro-1-oxo-propyl)-amino]-β-oxo-N-(2-thiazolyl)-benzene-propanamide melting at 204° C.

STEP C:
1,3-dihydro-3-methyl-1-(2-thiazolylimino)-furo[3,4-b]quinoline-9-ol

A mixture of 7 g of the product of Step B, 50 ml of tetrahydrofuran and 2.92 g of 4-dimethylamino-pyridine was refluxed for 24 hours and was cooled to room temperature and iced and vacuum filtered. The product was washed with tetrahydrofuran and dried under reduced pressure at 90° C. The product was stirred with 100 ml of water at room temperature and was vacuum filtered. The product was washed with water and dried under reduced pressure at 90° C. to obtain 3.5 g of 1,3-dihydro-3-methyl-1-(2-thiazolylimino)-furo[3,4-b]quinoline-9-ol melting at >270° C.

STEP D:
4-hydroxy-2-(1-hydroxyethyl)-N-(2-thiazolyl)-3-quinoline-carboxamide A mixture of 3.5 g of the product of Step C in 70 ml of 6N hydrochloric acid was heated at 50° C. for 7 hours and was cooled to room temperature and vacuum filtered. The product was washed with water and dried under reduced pressure at 90° C. to obtain 3.2 g of 4-hydroxy-2-(1-hydroxyethyl)-N-(2-thiazolyl)-3-quinoline-carboxamide hydrochloride. The product was added to 60 ml of water and the mixture was stirred at room temperature for one hour and vacuum filtered. The product was washed with water and dried under reduced pressure at 100° C. to obtain 2.75 g of 4-hydroxy-2-(1-hydroxyethyl)-N-(2-thiazolyl)3-quinoline-carboxamide with decompositions towards 270° C.

Analysis: Calculated: %C 57.13, %H 4.16, %N 13.32, %S 10.17. Found: %C 57.1, %H 4.2, %N 13.1, %S 9.9.

EXAMPLE 8

8-fluoro-4-hydroxy-2-(1-hydroxyethyl)-N-(2-thiazolyl)-3-quinoline-carboxamide

STEP A:
N-(2-fluorophenyl)-2-hydroxyimino-acetamide

A solution of 39.4 g of 2-fluoroaniline in 32.4 ml of concentrated hydrochloric acid and 215 ml of water and then a solution of 77.6 g of hydroxylamine hydrochloride in 355 ml of water were added to a mixture of 886 g of sodium sulfate hydrated with 10 moles of water, 64.55 g of chloral hydrate and 850 ml of water and the mixture was heated to reflux with stirring over 45 minutes and reflux was maintained for 5 minutes. The mixture was cooled to 25° C. and held there for 45 minutes. The product was washed with water and dried at room temperature and then at 70° C. under reduced pressure to obtain 56.8 g of N-(2-fluorophenyl)-2-hydroxyimino-acetamide melting at 120° C.

STEP B: 7-fluoro-1H-indole-2,3-dione 31.3 g of the product of Step A were added at 75°–77° C. over 65 minutes to 155 ml of concentrated sulfuric acid and the mixture was heated over 10 minutes to 90° C. and held there for 10 minutes and then cooled to 20° C. The mixture was poured into 750 g of ice and the mixture was stirred until the ice melted and was filtered. The filtrate was saturated with sodium chloride and was extracted several times with ethyl acetate. The combined organic phases were washed with aqueous saturated sodium chloride solution until the wash water was neutral, dried, filtered and evaporated to dryness under reduced pressure. The residue was dissolved in 350 ml of xylene at reflux and the hot solution was filtered and the filter was washed with 20 ml of boiling xylene. The filtrate was iced and vacuum filtered. The product was washed with xylene and dried under reduced pressure at 80° C. to obtain 12.85 g of 7-fluoro-1H-indole-2,3-dione melting at 198° C.

STEP C: 2-amino-3-fluoro-benzoic acid

A mixture of 19.27 g of the product of Step B and 197 ml of 10N sodium hydroxide solution was heated to 70° C. with stirring and heating was ceased to add 36.5 ml of 30% hydrogen peroxide over 20 minutes during which the temperature rose to 80° C. and descended to 70° C. At the end of the addition, the mixture was heated to 80° C. and held there for 10 minutes and then was cooled during which a mass formed. The latter was added to 200 ml of water with stirring and the pH was adjusted to 1 by addition of concentrated hydrochloric acid at a temperature less than 20° C. The mixture was stirred for 90 minutes and was vacuum filtered. The product was empasted twice with iced water and dried under reduced pressure at 70° C. The product was crystallized from 100 ml of a 1-1 ethanol-water mixture and 3 ml of acetic acid. The mixture was iced for one hour and was vacuum filtered. The product was empasted with a 1-1 ethanol-water mixture and dried at 70° C. under reduced pressure to obtain 14.8 g of 2-amino-3-fluoro-benzoic acid melting at 188° C.

STEP D:
2-(1-chloroethyl)-8-fluoro-4H-3,1-benzoxazine-4-one

A mixture of 9.3 g of 2-amino-3-fluoro-benzoic acid and 18,6 ml of α-chloropropionyl chloride was refluxed for 3 hours and excess acid chloride was distilled off. The residue was concentrated under reduced pressure at 70° C. for 2 hours to obtain 2-(1-chloroethyl)-8-fluoro-4H-3,1-benzoxazine-4-one which was used as is for the next step.

STEP E:
2-[(2-chloro-1-oxo-propyl)-amino]-β-oxo-N-(2-thiazolyl)-3-fluoro-benzene propanamide Using the procedure of Step A of Example 6, a solution of 17 g of N-(2-thiazolyl)-acetamide in 340 ml of tetrahydrofuran, 160 ml of butyllithium-hexane solution and 0.06 moles of the product of Step D in 130 ml of tetrahydrofuran were reacted to obtain 8.7 g of 2-[(2-chloro-1-oxo-propyl)amino]-β-oxo-N-(2-thiazolyl)-3-fluoro-benzene propanamide melting towards 170° C.

STEP F:
1,3-dihydro-3-ethyl-1-[(2-thiazolyl)-imino]-5-fluoro-furo[3,4-b]quinoline-9-ol Using the procedure of Step B of Example 6, 8.5 g of the product of Step E in 85 ml of tetrahydrofuran and 3.37 g of 4-dimethylamino-pyridine were reacted to obtain 6.5 g of 1,3-dihydro-3-ethyl-1-[(2-thiazolyl)-imino]-5-fluoro-furo[3,4-b]quinoline-9-ol melting towards 210° C.

STEP G:
8-fluoro-4-hydroxy-2-(1-hydroxyethyl)-N-(2-thiazolyl)-3-quinoline-carboxamide A mixture of 5 g of the product of Step F and 50 ml of 6N hydrochloric acid was heated at 50° C. for 5 hours and after addition of 50 ml of water, the mixture was cooled to 0° to 5° C. for 30 minutes and was vacuum filtered. The product was washed with water and dried under reduced pressure at 80° C. The product was successively chromatographed over silica gel twice and eluted with a 9-1 chloroform-methanol mixture to obtain 1.15 g of 8-fluoro-4-hydroxy-2-(1-hydroxyethyl)-N-(2-thiazolyl)-3-quinoline-carboxamide.

Analysis: Calculated: %C 54.05, %H 3.63, %F 5.70, %N 12.60, %S 9.62. Found: %C 53.7, %H 3.7, %F 5.7, %N 12.4, %S 9.4.

EXAMPLE 9

4-hydroxy-2-(1-hydroxypentyl)-N-(2-thiazolyl)-8-trifluoromethyl-3-quinoline-carboxamide

STEP A:
2-(1-chlorobutyl)-8-trifluoromethyl-4H-3,1-benzoxazine-4-one

A mixture of 10.25 g of 2-amino-3-trifluoromethyl-benzoic acid, 20 ml of toluene and 20.3 g of 2-chlorohexanoic acid chloride [prepared according to J. Org. CHem., Vol. 40 (1975), p. 23420] was refluxed for one hour and then toluene and excess acid chloride were removed by distillation. The residue was chromatographed over silica gel and eluted with methylene chloride and then by chromatography under pressure. Elution with a 1-1 ethyl acetate-petroleum ether (b.p.=60°–80° C.) mixture yielded 8.4 g of 2-(1-chlorobutyl)-8-trifluoromethyl-4H-3,1-benzoxazine-4-one in the form of an oil which was used as is for the next step.

STEP B:
2-[(2-chloro-1-oxo-pentyl)-amino]-β-oxo-N-(2-thiazolyl)-3-trifluoromethyl-benzene propanamide Using the procedure of Step A of Example 6, a solution of 6.94 g of N-(2-thiazolyl)-acetamide in 280 ml of tetrahydrofuran and 70 ml of a butyllithium-hexane solution and a solution of 7.8 g of the product of Step A in 40 ml of tetrahydrofuran were reacted to obtain 8.3 g of 2-[(2-chloro-1-oxo-pentyl)-amino]-β-oxo-N-(2-thiazolyl)-3-trifluoromethyl-benzene propanamide melting towards 184°–186° C.

STEP C:
3-butyl-1,3-dihydro-1-[(2-thiazolyl)-imino]-5-trifluoromethyl-furo[3,4-b]quinoline-9-ol Using the procedure of Step B in Example 6, a mixture of 7 g of the product of Step B, 70 ml of tetrahydrofuran and 2.2 g of 4-dimethylamino-pyridine were reacted to obtain 6.1 g of 3-butyl-1,3-dihydro-1-[(2-thiazolyl)-imino]-5-trifluoromethyl-furo[3,4-b]quinoline-9-ol melting at 228° C. (decomposition).

STEP D:
4-hydroxy-2-(1-hydroxypentyl)-N-(2-thiazolyl)-8-trifluoromethyl-3-quinoline-carboxamide A mixture of 6.1 g of the product of Step C, 60 ml of water and 60 ml of 6N hydrochloric acid was heated at 50° C. for 5 hours and was then cooled to room temperature and iced and vacuum filtered. The product was washed with water and added to 100 ml of water. The mixture was extracted with ethyl acetate and the organic phase was washed with water, dried, filtered and evaporated to dryness under reduced pressure. The 6.4 of residue was added to 50 ml of ether and the mixture was iced and vacuum filtered. The product was washed with ether and dried under reduced pressure at 60° C. to obtain 3.9 g of 4-hydroxy-2-(1-hydroxypentyl)-N-(2-thiazolyl)-8-trifluoromethyl-3-quinoline-carboxamide melting at 190° C.

EXAMPLE 10
4-hydroxy-2-(1-hydroxypropyl)-N-(2-thiazolyl)-8-trifluoromethyl-3-quinoline-carboxamide

STEP A:
2-(1-chloropropyl)-8-trifluoromethyl-4H-3,1-benzoxazine-4-one

A suspension of 20.3 g of 2-chloro-butyryl chloride and 12.3 g of 2-amino-3-trifluoromethyl-benzoic acid in toluene was refluxed under reduced pressure for one hour and was then evaporated to dryness under reduced pressure. The oil residue was added to 100 ml of iced water and the mixture was stirred for one hour and was vacuum filtered. The product was washed with water and dried under reduced pressure at 50° C. to obtain 17 g of 2-(1-chloropropyl)-8-trifluoromethyl-4H-3,1-benzoxazine-4-one melting at 65°–70° C.

STEP B:
2-[(2-chloro-1-oxo-butyl)-amino]-β-oxo-N-(2-thiazolyl)-3-trifluoromethyl-benzenepropanamide Using the procedure of Step A of Example 6, a solution of 16.58 g of N-(2-thiazolyl)-acetamide in 340 ml of tetrahydrofuran, 155 ml of a solution of butyllithium in hexane and a solution of 17 g of the product of Step A in 170 ml of tetrahydrofuran were reacted to obtain 5.5 g of 2-[(2-chloro-1-oxo-butyl)-amino]-β-oxo-N-(2-thiazolyl)-3-trifluoromethyl-benzenepropanamide melting at 170° C.

STEP C:
1,3-dihydro-3-ethyl-1-[(2-thiazolyl)-imino]-5-trifluoromethyl-furo[3,4-b]quinoline-9-ol A solution of 1 g of the product of Step B in 20 ml of tetrahydrofuran and 0.34 g of 4-dimethylamino-pyridine was refluxed for 90 minutes and was evaporated to dryness under reduced pressure. The residue was added to 10 ml of water and was vacuum filtered. The product was dried under reduced pressure at 90° C. to obtain 0.8 g of 1,3-dihydro-3-ethyl-1-[(2-thiazolyl)-imino]-5-trifluoromethyl-furo[3,4-b]quinoline-9-ol melting towards 250°–260° C.

STEP D:
4-hyddroxy-2-(1-hydroxy-propyl)-N-(2-thiazolyl)-8-trifluoromethyl-3-quinoline-carboxamide A mixture of 4 g of the compound of Step B and 40 ml of 6N hydrochloric acid was heated at 50° C. for 4 hours and was then cooled and vacuum filtered. The product was washed with water and dried under reduced pressure at 100° C. to obtain 4.15 g of 4-hydroxy-2-(1-hydroxy-propyl)-N-(2-thiazolyl)-8-trifluoromethyl-3-quinoline-carboxamide hydrochloride. A mixture of 1.8 g of the said compound, 36 ml of absolute ethanol and 4.1 ml of 1N potassium hydroxide in methanol was stirred at room temperature for 2 hours and was filtered. The filtrate was evaporated to dryness under reduced pressure and the residue was taken up in 10 ml of tetrahydrofuran. The solution was dried and evaporated to dryness under reduced pressure. The residue was taken up in 5 ml of isopropyl ether and the mixture was vacuum filtered. The product was dried under reduced pressure at 70° C. to obtain 0.81 g of 4-hydroxy-2-(1-hydroxy-propyl)-N-(2-thiazolyl)-8-trifluoromethyl-3-quinoline-carboxamide. 0.53 g of the product were recovered by empasting the insolubles with tetrahydrofuran.

Analysis: Calculated: %C 52.38, %H 3.55, %F 14.34, %N 10.57, %S 8.07. Found: %C 51.2, %H 3.5, %F 14.5, %N 10.6, %S 8.1.

EXAMPLE 11
4-hydroxy-2-(1-hydroxy-ethyl)-N-(2-thiazolyl)-8-trifluoromethyl-3-quinoline-carboxamide

STEP A:
1,3-dihydro-3-methyl-1-[(2-thiazolyl)-imino]-5-trifluoromethyl-furo[3,4-b]quinoline-9-ol A mixture of 6 g of 2-(1-chloroethyl)-4-hydroxy-N-(2-thiazolyl)-8-trifluoromethyl-3-quinoline-carboxamide [described in Examples 5 and 14 of U.S. patent application Ser. No. 262,952] and 50 ml of acetic acid was placed in an oil bath heated to 140° C. and held there for 9 minutes and then cooled to room temperature. The mixture was held at 16° C. for one hour and was vacuum filtered. The product was washed with acetic acid, then with ether and dried under reduced pressure at 80° C. to obtain 5.4 g of 1,3-dihydro-3-methyl-1-[(2-thiazolyl)-imino]-5-trifluoromethyl-furo[3,4-b]quinoline-9-ol in the form of an acetate. The latter was added to 100 water to which was added an aqueous saturated sodium bicarbonate solution to adjust the pH to 6. The mixture was vacuum filtered and the product was washed with water and dried under reduced pressure at 70° C. to obtain 4.2 g of 1,3-dihydro-3-methyl-1-

[(2-thiazolyl)-imino]-5-trifluoromethyl-furo[3,4-b]quinoline-9-ol melting at 260° C. (decomposition).

STEP B:
4-hydroxy-2-(1-hydroxyethyl)-N-(2-thiazolyl)-8-trifluoromethyl-3-quinoline-carboxamide Using the procedure of Step D of Example 10, 3 g of the product of Step A were reacted to obtain 1.5 g of 4-hydroxy-2-(1-hydroxyethyl)-N-(2-thiazolyl)-8-trifluoromethyl-3-quinoline-carboxamide melting at 205° C. and then at 235° C. The product had the same characteristics of the compound of Example 2.

Other compounds of the invention include 4-hydroxy-2-(1-hydroxybutyl)-N-(2-thiazolyl)-8-trifluoromethyl-3-quinoline-carboxamide melting at 180° C. and 4-hydroxy-2-(1-hydroxy-2-methyl-propyl)-N-(2-thiazolyl)-8-trifluoromethyl-3-quinoline-carboxamide melting at 220° C.

EXAMPLE 12

Tablets were prepared from 50 mg of the product of Example 2 or 30 mg of the product of Example 10 and sufficient excipient of lactose, starch, talc and magnesium stearate for a final tablet weight of 350 mg.

PHARMACOLOGICAL DATA

A. Analgesic Activity

The test was based on that of Koster et al [Fed. Proc., Vol. 1B (1959), p. 412] in which mice received an intraperitoneal injection of acetic acid to provoke repeated stretching and twisting movements which persist for more than 6 hours. An analgesic prevents or reduces this syndrome which is considered to be an exteriorization of a diffuse abdominal pain. A 1% solution of acetic acid in water was used and the dose relieving the syndrome under these conditions was 0.01 ml/g or 100 mg/kg of acetic acid.

The test compound was orally administered to the mice 30 minutes before the acetic acid injection and the mice had been fasting for the previous 24 hours. The stretching were counted for each mouse for a 15 minute observation period after the acetic acid injection and the dose which diminished the number of stretchings by 50% as compared to the controls ($DA_{50}$) was 1.2 and 0.3 mg/kg for the compounds of Example 2 and 10 respectively.

B. Anti-inflammatory Activity

The anti-inflammatory activity was determined by the edema test provoked by carraghenin in male rats weighing about 130 to 150 g which received 0.05 ml of sterile suspension of 1% carraghenin into the tibiotarsien articulation of the rear paw. Simultaneously the test product in a suspension of 0.25% carboxymethyl cellulose and 0.02% of Tween was orally administered. The volume of the paw was measured before the test and then 2, 4, 6, 8 and 24 hours later. The intensity of inflammation was maximum at 4 to 6 hours after the injection of carraghenin and the differences in paw volume of controls and treated animals were evidence of anti-inflammatory action. The $DA_{50}$ dose which is that which reduced the edema by 50% was 15 and 12 mg/kg for the products of Examples 2 and 10 respectively.

Various modifications of the products and processes of the invention may be made without departing from the spirit or scope thereof and it is to be understood that the invention is intended to be limited only as defined in the appended claims.

What we claim is:

1. A compound of the formula

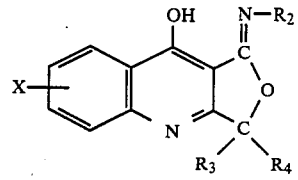

wherein X is in the 5, 6, 7 or 8-position and is selected from the group consisting of hydrogen, halogen, alkyl of 1 to 5 carbon atoms, alkoxy of 1 to 4 carbon atoms, —$CF_3$, —$OCF_3$ —$SCF_3$, $R_2$ is selected from the group consisting of a heterocycle connected to the nitrogen atom by a carbon atom selected from thiazolyl, 4,5-dihydro-thiazolyl, pyridinyl, oxazolyl, isoxazolyl or imidazolyl, all optionally substituted with alkyl of 1 to 4 carbon atoms and phenyl optionally substituted with one or two members of the group consisting of —OH, alkyl of 1 to 4 carbon atoms, alkoxy of 1 to 4 carbons, —$CF_3$, —$NO_2$ or halogen, $R_3$ is selected from the group consisting of hydrogen, alkyl of 1 to 4 carbon atoms, phenyl or naphthyl, and $R_4$ is selected from the group consisting of hydrogen, alkyl of 1 to 4 carbon atoms, phenyl or naphthyl.

* * * * *